US009341618B2

(12) United States Patent
Sasajima et al.

(10) Patent No.: US 9,341,618 B2
(45) Date of Patent: May 17, 2016

(54) METHOD FOR EVALUATING OR SCREENING HAIR GROWTH-REGULATING AGENT

(75) Inventors: Michiyo Sasajima, Tochigi (JP); Noriko Ito, Tochigi (JP); Shigeru Moriwaki, Tochigi (JP); Chie Fuse, Tochigi (JP)

(73) Assignee: Kao Corporation, Tokyo (JP)

(*) Notice: Subject to any disclaimer, the term of this patent is extended or adjusted under 35 U.S.C. 154(b) by 1056 days.

(21) Appl. No.: 12/033,601

(22) Filed: Feb. 19, 2008

(65) Prior Publication Data

US 2008/0206806 A1    Aug. 28, 2008

(30) Foreign Application Priority Data

Feb. 22, 2007  (JP) ................. 2007-042560
Nov. 14, 2007  (JP) ................. 2007-295220
Dec. 28, 2007  (JP) ................. 2007-338801

(51) Int. Cl.
*C12Q 1/02*    (2006.01)
*G01N 33/50*   (2006.01)

(52) U.S. Cl.
CPC .................. *G01N 33/5082* (2013.01)

(58) Field of Classification Search
CPC ............................................. G01N 33/5082
USPC ........................................................ 435/29
See application file for complete search history.

(56) References Cited

U.S. PATENT DOCUMENTS

2008/0138850 A1    6/2008  Vielhaber et al.

FOREIGN PATENT DOCUMENTS

| EP | P 1 096 255 A2 | 5/2001 |
| EP | 1 939 279 A1 | 7/2008 |
| EP | 06125283.9 | 7/2008 |
| JP | 08-043375 | 2/1996 |
| JP | 11-049647 | 2/1999 |
| JP | 2002-062289 | 2/2002 |
| JP | 2005-206536 | 8/2005 |
| JP | 2006-008657 | 1/2006 |

OTHER PUBLICATIONS

Messenger et al., Minoxidil: mechanisms of action on hair growth, British Journal of Dermatology, vol. 150, 2004, p. 186-194.*
Jankovic et al., The Control of hair growth, Dermatology Online Journal vol. 4, 1998.*
Ebling, F.J.G., "Hair Follicles and Associated Glands as Androgen Targets," *Clin. Endocrinol. Metab.* 15:319-339, W.B. Saunders (1986).
Jindo, T., et al., "Organ Culture of Mouse Vibrissal Hair Follicles in Serum-Free Medium," *J. Dermatol.* 20:756-762, Japanese Dermatological Association (1993).
Sasajima, M., "The Mechanism of Hair Growth Promotion by t-flavanone," *Fragr. J.* 33:36-43, Fragrance Journal Company Limited (2005).
Philpott, M.P., et al., "Human Hair Growth In Vitro," *J. Cell. Sci.* 97:463-471, Company of Biologists (1990).
Stenn, K.S. and Paus, R., "Controls of Hair Follicle Cycling," *Physiol. Rev.* 81:449-494, American Physiological Society (2001).
Uzuka, M. and Hanzawa, C., "Adult Mouse Vibrissa Follicles in Organ Culture: Effects of Growth Factors and Drugs on Hair Growth," *Jpn. J. Dermatol.* 104: 979-987, Japanese Dermatological Association (1994).
English Language Abstract for JP 11-049647, Patent Abstracts of Japan (listed on accompanying document PTO/SB/08A as document FP1).
English Language Abstract for JP 2002-062289, Patent Abstracts of Japan (listed on accompanying document PTO/SB/08A as document FP2).
English Language Abstract for JP 2005-206536, Patent Abstracts of Japan (listed on accompanying document PTO/SB/08A as document FP3).
English Language Abstract for JP 2006-008657, Patent Abstracts of Japan (listed on accompanying document PTO/SB/08A as document FP4).
Database Biosis, Accession No. PREV200600549949, English Language Abstract of Zhang, H., et al., "Effect of latanoprost on pig hair follicles in vitro," *Zhonghua Pifuke Zazhi (Chin. J. Dermatol.)* 39:391-393 (Jul. 2006), 1 page.
Database Biosis, Accession No. PREV200510042048, English Language Abstract of Zhang, X-H., et al., "Effect of some traditional Chinese herbs on hair growth of pig hair follicle in vitro," (*Chin. J. Dermatol.*) 38:102-104 (2005), 1 page.
Database Biosis, Accession No. PREV200510310797, English Language Abstract of Zhou, N-H., et al., "Expression of VEGF eukaryotic expression vector in HaCaT cells and its biological effects," (*Chin. J. Dermatol.*) 38:439-441, (2005) 1 page.
Extended European Search Report for European Application No. EP 08151644.5-2404, mailed on May 23, 2008, European Patent Office, Munich, Germany.
Office Action issued for corresponding Japanese application No. 2007-338801, mailed May 19, 2009 by the Japanese Patent Office.
Hotta, M et al., "Effect of t-flavanone on hair growth," Fragrance J 31(2); 33-40 (2003), Fragrance Company Ltd., Tokyo, Japan.
Soma, T et al., "Involvement of transforming growth factor-beta2 in catagen induction during the human hair cycle," J Invest Dermatol 118(6): 993-7 (Jun. 2002), Blackwell Publishing Inc., Malden, MA.
Taylor, M et al., "Cyclosporin A prolongs human hair growth in vitro," J Invest Dermatol 100(3): 237-9 (Mar. 1993), Blackwell Publishing Inc., Malden, MA.

(Continued)

*Primary Examiner* — Taeyoon Kim
*Assistant Examiner* — Tiffany Gough
(74) *Attorney, Agent, or Firm* — Sterne, Kessler, Goldstein & Fox P.L.L.C.

(57) ABSTRACT

The present invention provides a method for evaluating or screening a hair growth-regulating agent which utilizes a readily available animal.
The present invention is directed to a method for evaluating or screening a hair growth-regulating agent which comprises subjecting hair follicles of a pig to an organ culture in the presence of a test substance, and evaluating or selecting a substance which promotes or suppresses the growth of the hair follicles.

7 Claims, No Drawings

(56) References Cited

OTHER PUBLICATIONS

Zhang, H., et al., "Effect of latanoprost on pig hair follicles in vitro," *Zhonghua Pifuke Zazhi* (*Chin. J. Dermatol.*) 39:391-393 (Jul. 2006).

Zhang, X-H., et al., "Effect of some traditional Chinese herbs on hair growth of pig hair follicle in vitro," *Zhongua Pifuke Zazhi* (*Chin. J. Dermatol.*) 38:102-104 (2005).

Zhou, N-H., et al., "Expression of VEGF eukaryotic expression vector in HaCaT cells and its biological effects," *Zhongua Pifuke Zazhi* (*Chin. J. Dermatol.*) 38:439-441, (2005).

Fan W., et al., "The new model for the study of hair biology—the culture of pig hair vollicles in vitro," *J. Clin. Dermatol.* 31:677-680 (2002).

Feneis, H., ed., "Illustrated Anatomical Dictionary," $2^{nd}$ Edition, 1983, pp. 396-397, Igaku-Syoin Ltd., Tokyo, Japan, publisher.

"Anatomical Terms of Location," from web.archive.org/web/20071022135947/en.wikipedia.org/wiki/Anatomical_terms_of_location, last modified Oct. 16, 2007.

"Abdomen" from en.wikipedia.org/wiki/Abdomen, last modified Dec. 2, 2010.

Communication of a notice of opposition in EP Application No. 08151644.5, dated May 27, 2011, European Patent Office, Munich, Germany.

EP Opposition document D3: Hibino, T. et al., "Role of TGF-beta2 in the human hair cycle," J Dermatol Sci, Jun. 2004; 35(1): 9-18, Elsevier, Netherlands.

EP Opposition document D7: "Minoxidil,"—Wikipedia entry from http://de.wikipedia.org/wiki/Minoxidil, printed May 22, 2011 (4 pages).

EP Opposition document D8: "Minoxidil," RÖMPP Online—version 3.13, ID=RD-13-02566, Aug. 2006, George Thieme Verlag, Germany.

EP Opposition document D9: "Hausschwein"—Wikipedia entry from http://de.wikipedia.org/wiki/Hausschwein, printed May 11, 2004 (5 pages) plus Datei:Sow with piglet.jpg from http://de.wikipedia.org/w/index/php?title=Datei:Sow_with_piglet.jpg &filetimestamp=. . . (1 pages) printed May 11, 2011.

Office action for Chinese Patent Application No. 200810080430.3, mailed Feb. 17, 2012 from the Patent Office of the People's Republic of China, Beijing, China.

Applicant's Reply dated Dec. 21, 2011, to the Communication of notices of opposition dated Jun. 16, 2011, and the notice of opposition filed by the third party on May 17, 2011, against European Patent No. 1962090, filed with the European Patent Office, Munich, Germany.

"Experimental Report," filed by Patentee of European Patent No. 1962090 as document D10 with Applicant's Reply dated Dec. 21, 2011, filed with the European Patent Office, Munich, Germany.

Summons to attend oral proceedings pursuant to Rule 115(1) EPC, issued Sep. 25, 2012 for European Patent No. 1962090, European Patent Office, Munich, Germany.

\* cited by examiner

METHOD FOR EVALUATING OR SCREENING HAIR GROWTH-REGULATING AGENT

FIELD OF THE INVENTION

The present invention relates to a method for evaluating or screening a hair growth-regulating agent utilizing hair follicles of pigs.

BACKGROUND OF THE INVENTION

Generally, regarding hair, many people want growth or growth-suppression of hair depending on the site of the hair. For example, not a few people have a problem with regard to hair such as thinning hair or baldness caused by stress, genetics or the like. In addition, some people feel troublesome in so-called depilation.

It is known that there are two kinds of hairs, i.e. a hair which depends on a male hormone and a hair which does not depend thereon. For example, it is believed that male alopecia in which baldness or receding of hairline occurs in the region between the front of head and the top of head, beard, the hair at legs and underarm hair are deeply related to male hormones, whereas the hair in the temporal region of head, hair at the back of head, eyebrows, and eyelashes are less relevant to male hormones (Non-Patent Document 1: Ebling F. J. et al., Clin. Endocrinol Metab., Vol. 15, 319-339 (1986), Non-Patent Document 2: Sternn K. S. et al., Physiol. Rev., Vol. 81, 449-494 (1993)).

Thus, hair-growth agents and hair growth-suppressing agents which regulate growth of hair have been developed from various aspects (Patent Document 1: JP 2005-206536 A, Patent Document 2: JP 2006-8657 A).

Recently, for the search of hair growth agents and hair growth-suppressing agents, there have been used a method of a cell culture of hair follicles of humans, mice or rats, or a method of an organ culture of the hair follicles because these methods can rapidly and conveniently evaluate or screen these agents (Patent Document 3: JP 11-49647 A; Patent document 4: JP 2002-62289 A; Non-Patent Document 3: T. Jindo et al., The Journal of Dermatology, Vol. 20, 756-762, 1993; Non-Patent Document 4: Makoto Uzuka & Tika Souzawa, Nippi Kaishi, 104(8), 979-987, 1994; Non-Patent Document 5: M. P. Philpott et al., Journal of Cell Science, 97, 463-471, 1990). Screening through an organ culture of hair follicles of humans is highly reliable in data but has a difficulty in obtaining hair follicles of humans and thus is not suitable for mass screening. Although hair follicles of mice and rats are always available, screening through an organ culture of hair follicles of mice and rats is also not suitable for mass screening in view of animal protection because the method uses laboratory animals.

SUMMARY OF THE INVENTION

The present invention provides a method for evaluating or screening a hair growth-regulating agent which includes subjecting hair follicles of a pig to an organ culture in the presence of a test substance, and evaluating or selecting a substance which promotes or suppresses the growth of the hair follicles.

The present invention also provides a method for evaluating or screening a hair growth-regulating agent for male hormone-dependent hairs which includes subjecting hair follicles in the abdominal region or the dorsal region of a pig to an organ culture in the presence of a test substance, and evaluating or selecting a substance which promotes or suppresses the growth of the hair follicles.

The present invention also provides a method for evaluating or screening a hair growth agent for male alopecia which includes subjecting hair follicles in the abdominal region of a pig to an organ culture in the presence of a test substance, and evaluating or selecting a substance which promotes the growth of the hair follicles.

The present invention also provides a method for evaluating or screening a hair growth-suppressing agent for male hormone-dependent hairs which includes subjecting hair follicles in the dorsal region of a pig to an organ culture in the presence of a test substance, and evaluating or selecting a substance which suppresses the growth of the hair follicles.

The present invention also provides a method for evaluating or screening a hair growth-regulating agent that acts without the intervention of the action of a male hormone which includes subjecting hair follicles in the lateral region, inguinal region, shoulder or buttocks of a pig to an organ culture in the presence of a test substance, and evaluating or selecting a substance which promotes or suppresses the growth of the hair follicles.

DETAILED DESCRIPTION OF THE INVENTION

The present invention relates to provision of a method for evaluating or screening a hair growth-regulating agent which utilizes readily available hair follicles of an animal.

The present inventors have made researches on a novel evaluation or screening system for hair growth-regulating substances and have found, upon subjecting hair follicles at various sites of a pig to an organ culture, that there are two kinds of hair follicles, i.e. hair follicles in which the growth thereof is affected by 5α-dihydrotestosterone (hereinafter, referred to as DHT) and those in which the growth thereof is not affected by DHT, and found that a hair growth-regulating agent for male hormone-dependent hairs or male hormone-nondependent hairs can be evaluated or screened by utilizing the fact.

According to the present invention, it is possible to conveniently and effectively evaluate or select a substance which exhibits a hair growth-promoting or hair growth-suppressing effect because hair follicles of a pork pig are readily available in a large amount.

The method for evaluating or screening a hair growth-regulating agent according to the present invention includes subjecting the hair follicles at a specific site of a pig to an organ culture, and evaluating or screening a substance which promotes or suppresses the growth thereof.

As shown in the examples described below, when hair follicles at each site of a pig are subjected to an organ culture in the presence of one of male hormones, DHT, and the hair growth of the hair follicles at a site of the pig is compared in terms of a hair elongation quantity with that at the same site not added with DHT, the elongation quantity of the hair follicles in an abdominal region largely decreased, that in a dorsal region largely increased, and those in a lateral region, inguinal region, shoulder and buttocks were approximately the same (Example 1). Namely, it was found that the growth of hair follicles of a pig was affected or not affected by DHT depending on the site at which the hair follicles were taken.

On the other hand, with regard to humans, it has long been known that the symptom of male alopecia in which baldness or receding of hairline occurs in the region between the front of head and the top of head is made progress by a male hormone and that an antiandrogen is effective therefor.

It was reported that the growth each of beard and hair at legs was promoted by a male hormone (Ebling F. J. et al., Clin. Endocrinol Metab., Vol. 15, 319-339 (1986)), and it has been believed that hairs in the temporal region of head and back of head, eyebrows, and eyelashes are less affected by male hormones (Stenn K. S. et al., Physiol. Rev., Vol. 81, 449-494 (2001)).

Accordingly, it is considered that the growth of hair follicles in the abdominal region of a pig resembles the growth of the hairs which are male hormone-dependent and are suppressed by a male hormone, such as hair in the region between the front of head and the top of head of a human, the growth of hair follicles in the dorsal region of a pig resembles the growth of the hairs which are male hormone-dependent and are promoted by a male hormone, such as beard, hair at the legs, chest hair, hair of pubis, and underarm hair at puberty of a human, and the growth of hair follicles in the lateral region, inguinal region, shoulder and buttocks of a pig resembles the growth of the hairs which are not affected by a male hormone, such as hair in the temporal region of the head or at the back of the head, eyebrows, eyelashes, or underarm hair after puberty of a human.

Therefore, it is considered to be possible to evaluate or screen hair growth-regulating agents such as a male hormone-dependent hair growth-regulating agent, a hair growth agent for male alopecia, a male hormone-dependent hair-suppressing agent, and a male hormone-nondependent hair growth-regulating agent by utilizing as an indicator the growth of the hair follicles at a specific site of a pig.

The evaluation or screening method according to the present invention can be carried out according to the following steps (1) through (3):

(1) a step of contacting hair follicles at the specific site of a pig with a test substance,
(2) a step of subjecting said hair follicles to an organ culture, measuring the growth of the hair follicles, and comparing said growth with the growth of hair follicles which have not been contacted with the test substance, and
(3) a step of evaluating or selecting as a hair growth-regulating agent a test substance which promotes or suppresses the growth of the hair follicles based on the results of step (2).

The hair follicle of a pig refers to a tissue surrounding the whole part of the hair root taken from the skin of a pig, and specifically refers to the whole tissue including organs that participate in elongation of hair, such as hair shaft, hair papilla, hair matrix cell, hair root and the like.

In the present invention, hair follicles in the growing phase (growing phase hair follicles) are used among these hair follicles.

The pig from which the hair follicles are taken may be of any breed as long as it has hair, and generally pig breeds crossed for meat can be used.

Examples of pigs improved for meat include Yorkshire breeds having white hair (there are three types, i.e. large, medium and small types) which are obtained by crossing a native pig in the district of Yorkshire, England, with a Chinese breed, Neapolitan breed, Lester breed and the like; Berkshire breeds having black hair obtained by crossing a native pig in the districts of Berkshire and Wilshire, England, with a Siamese breed, Chinese breed and Neapolitan breed; Landrace breeds having white hair obtained by crossing a native Danish pig with a Large Yorkshire breed; Hampshire breeds having black hair originally come from the commonwealth of Massachusetts or Kentucky, USA; and Duroc breeds originated in USA from a red-coloured pig originally came from Europe and a red-coloured pig improved in New Jersey.

Registered breeds genealogically maintained in Japan include six breeds including Medium Yorkshire breeds, Berkshire breeds (B), Landrace breeds (L), Large Yorkshire breeds (W), Hampshire breeds (H) and Duroc breeds (D). Many of common pork pigs are crossbreeds of these breeds combined with each other except for black pigs of pure Berkshire breeds, and include, for example, "Tochigi LaLa pork" which is obtained by crossing "LW sow", obtained by crossing "Tochigi L" that is a Landrace (L)-inherited pig with a Large Yorkshire breed (W), with a Duroc breed (D); and "Tokyo X" which is obtained by crossing a Peking black pig with a Berkshire breed and a Duroc breed.

Among these, it is preferable to use breeds having white hair such as Yorkshire breeds and Landrace breeds whose hair in the growth phase is easy to distinguish from the other hair, and crossbreeds thereof. When a pork pig is used, it is possible to obtain hair follicles from the skin of the pig after the meat is taken out, which is preferable because an animal is not injured only for the purpose of obtaining hair follicles.

Examples of the sites of a pig to be used include an abdominal region, dorsal region, lateral region, inguinal region, shoulder and buttocks, and the site is selected depending on the purpose of evaluation. Namely, it is preferable to use hair follicles in an abdominal region for evaluation or screening of a hair growth agent for male alopecia, hair follicles in a dorsal region for evaluation or screening of a hair growth-regulating (promoting or suppressing) agent for male hormone-dependent hairs such as beard or hair at arms, legs, chest, pubic region, underarm at puberty and hair follicles in a lateral region, inguinal region, shoulder or buttocks for evaluation or screening of a hair growth-regulating (promoting or suppressing) agent for male hormone-nondependent hairs such as hair at human temporal, occipital, eyebrows, eyelashes or underarm after puberty.

For collecting hair follicles, the skin of a pig at a site selected in compliance with the evaluation purpose may be cut out, and after removing fat tissue under aseptic conditions, hair follicles may be isolated.

Contact of hair follicles with a test substance can be effected by, for example, preliminarily adding the test substance to a culture medium to give a predetermined concentration of the test substance, placing the hair follicles in the resulting culture medium, or, alternatively, by adding the test substance to a culture medium in which the hair follicles have been placed so that the culture medium contains a predetermined concentration of the test substance.

The organ culture of hair follicles may be effected according to a known method for an organ culture of hair follicles such as an organ culture of hair follicles of vibrissa of a mouse (Non-Patent Document 4), by, for example, placing collected hair follicles on a dish such as a sterile mesh soaked in a culture medium, and incubating at 37° C. usually for 2 to 56 days, preferably 4 to 21 days, in an air phase containing $CO_2$.

Examples of culture media include RPMI 1640 medium, William's E medium, and DMEM/Ham F12 (1:1) medium, and agar and gelatine may be optionally added. If necessary, antibiotics, amino acids, blood serum, growth factors, extracts from a living body and the like may be added.

Examples of methods for measuring the growth of hair follicles include a method of measuring increase or decrease of the elongation quantity or gauge of hair by using an image analysis or a micrometer under a microscope, a method of measuring a cell proliferation activity or the number of proliferating cells in the hair follicles after the organ culture, and a method of measuring apoptotic cells predominantly found in hair follicles inversely proportional to the growth strength of the hair follicles.

When a method of measuring increase or decrease of the elongation quantity or gauge of hair by using an image analysis or a micrometer under a microscope is used for measuring the growth of hair follicles, it is possible, for example, to calculate a hair elongation quantity after the commencement of the organ culture by measuring the length from the base of hairbulb to the tip of hair shaft, or to calculate the increase or decrease of the gauge of the hair after the commencement of the organ culture by comparing the gauge of the elongated hair shaft each at the tip thereof and in the vicinity of the root thereof.

In the above case, a substance that promotes or suppresses the growth of hair follicles may be evaluated by contacting the hair follicles with a test substance, culturing the hair follicles, comparing the measured elongation quantity or gauge of the hair with the elongation quantity or gauge of the hair not contacted with the test substance (control), calculating an elongation rate (%) or a gauge variation rate (%) regarding the rate of the control as 100, and evaluating the test substance based on the results. A higher value is evaluated to promote hair growth and a lower value is evaluated to suppress hair growth.

When a cell proliferation activity, a cell respiratory activity or the number of proliferating cells in hair follicles is measured, it is possible, for example, to measure a cell proliferation activity by adding bromodeoxyuridine to the medium used for an organ culture and calculating a DNA synthesis ability from the incorporation quantity of the bromodeoxyuridine in DNA, or measure a cell respiratory activity by means of an Alamar Blue assay or MTT assay (a method in which a tetrazolium salt added as a substrate is reduced by NADH in mitochondria and an absorbancy or fluorescence of the resulting product is measured), or measure the number of proliferating cells by dyeing with an antibody of a proliferation cell marker, Ki67 or PCNA (Proliferation Cell Nuclear Antigen).

In the above case, evaluation of a substance that promotes or suppresses the growth of hair follicles may be conducted by contacting the hair follicles with a test substance, culturing the hair follicles, comparing a cell proliferation activity or the number of proliferating cells measured as in the above with a cell proliferation activity or the number of proliferating cells of hair follicles not contacted with the test substance (control), calculating a proliferation activity ratio (%) or a proliferating cell ratio (%) regarding that of the control as 100, and evaluating the test substance based on the results. A higher value is evaluated to promote hair growth and a lower value is evaluated to suppress hair growth.

In the case where apoptotic cells in hair follicles are measured, it is possible to measure the number of apoptotic cell by measuring the quantity of fragmented DNA during progress of apoptosis or by TUNEL method.

In the above case, a substance that promotes or suppresses the growth of hair follicles may be evaluated by contacting the hair follicles with a test substance, culturing the hair follicles, comparing the quantity of fragmented DNA or the number of apoptotic cell measured as in the above with a quantity of fragmented DNA or the number of apoptotic cell of hair follicles not contacted with the test substance (control), calculating a ratio of a quantity of fragmented DNA (%) or a ratio of the number of apoptotic cell (%) regarding each ratio of the control as 100, and evaluating the test substance based on the results. A higher value is evaluated to promote hair growth and a lower value is evaluated to suppress hair growth.

EXAMPLE

Example 1

(1) Isolation of Hair Follicles

As a pig skin, a skin obtained from a crossbred pig with white hair which has been bred as a pork pig in Japan was used. The pig skin was cut into an appropriate size, the extra fat was cut away, and the resulting skin was soaked in a Hibiten solution (5% Hibiten solution (Sumitomo Pharmaceuticals) was diluted to 5 to 20 times with water) for 5 to 10 minutes under sterile conditions for sterilization and then washed several times with D-PBS.

Then hair follicles were isolated from the treated pig skin using forceps and scalpel (FEATHER No. 10) under a stereo microscope and collected in a medium. RPMI1640 medium (Gibco cat. No. 11835-030), William's E medium (Gibco cat. No. 12551-032) and DMEM/HamF12 (1:1) medium (Gibco cat. No. 11039-021) were used as the medium.

(2) Influence of DHT on Organ Culture of Hair Follicles of Pig

According to the procedures (1), hair follicles of a pig were obtained from the dorsal region, lateral region, abdominal region, inguinal region, buttocks and shoulder of the pig. The isolated hair follicles were placed in a 24-well culture plate to give one hair follicle per well. As a medium, William's E medium (Gibco cat. No. 12551-032) was used in an amount of 400 μL per well. One % of a penicillin/streptomycin solution (Gibco cat. No. 15140-122) was added to the medium for the subsequent use.

The William's E medium was used and DHT (Sigma cat. No. A-8380) was added in such an amount as to give a final concentration of 10 ng/ml in the medium. Incubation was carried out at 37° C. for 6 days in an incubator containing 5% of $CO_2$.

The medium was exchanged every two days or every three days, and a hair elongation quantity after 6 days incubation was measured and compared with that of control.

For the control, William's E medium not containing DHT was used, and a hair elongation quantity after the organ culture was regarded as 100%.

Incidentally, a hair elongation quantity was measured, regarding the date on which incubation was commenced as the $0^{th}$ day, by taking stereo microscopic images with a CCD camera (pixera model No. PVC 100C) at the $0^{th}$ day and the $6^{th}$ day, and measuring the change of the length from the base of hairbulb to the tip of hair shaft based on the images.

TABLE 1

| The site at which hair follicle was taken | DHT (10 ng/mL)* |
|---|---|
| Dorsal region | 179% |
| Lateral region | 108% |
| Abdominal region | 75% |
| Inguinal region | 102% |
| Shoulder | 99% |
| Buttocks | 102% |

*A hair elongation quantity was measured at the $6^{th}$ day of the organ culture. The control was regarded as 100%.

From Table 1, it was shown that DHT affected even the growth of hair follicles of a pig, and that the degree of the influence of DHT varied depending on the site of the hair follicles.

The growth of hair follicles in the abdominal region was suppressed by DHT, indicating that an elongation-promoting agent for the hair follicles can be a useful hair growth agent for male alopecia.

The growth of hair follicles in the dorsal region was promoted by DHT, indicating that an elongation-suppressing agent for the hair follicles can be a hair growth-suppressing agent for the hair which is male hormone-dependent and whose growth is promoted by a male hormone.

The hair follicles at the other sites were less influenced by DHT, indicating that an elongation-promoting or elongation-suppressing agent for the hair follicles can be a hair growth agent or a hair growth-suppressing agent which acts without the intervention of the action of a male hormone.

Example 2

Evaluation of Hair Growth-Regulating Agents (1)
t-Flavanone and TGF-β2

Similarly to Example 1, hair follicles at the buttocks of a pig were obtained. RPMI1640 medium (Gibco cat. No. 11835-030) was used for the culture. One % of penicillin/streptomycin (Gibco cat. No. 15140-122) solution was added to the RPMI1640 medium.

The above-mentioned RPMI1640 medium was incorporated with t-flavanone (trans-3,4'-dimethyl-3-hydroxyflavanone (Hotta et al., Flagrance Journal, Vol. 31, No. 2, 33-40 (2003)) which is a useful ingredient of a medicated cosmetic hair growth agent and is confirmed to promote hair growth by an organ culture of the hair follicles of the vibrissa of a rat, so that it is contained in the medium at a final concentration of 1 μM (as to a synthesis method, see JP 2000-198779). Another medium was incorporated with TGF-β2 (R & D Systems, Inc., item No. 102-B2-001/CF) which is confirmed to suppress hair growth by an organ culture of hair follicles of a human (Philpott et al., J. Cell Sci., Vol. 97, 463-47 (1990); Soma et al., J. Invest Dermatol, Vol. 118, 993-997 (2002)) so that it is contained in the medium in an amount of 10 ng/mL.

The hair follicles were incubated at 37° C. for 8 days in an incubator containing 5% of $CO_2$. The medium was exchanged every two days or every three days, and a hair elongation quantity after 8 days incubation was measured and compared with that of a control.

For evaluation of the growth quantity of the hair follicles, a method similar to that of Example 1 was used. For the control, RPMI1640 medium not containing a test substance was used, and a hair elongation quantity after the organ culture was regarded as 100%.

TABLE 2

| Test substance | Hair elongation rate (%) when that of control is regarded as 100% |
|---|---|
| t-Flavanone (1 μM) | 145 |
| TGF-β2 (10 ng/mL) | 59 |

The 8th day of organ culture in RPMI1640 medium

It was confirmed that use of t-flavanone exhibited hair elongation promotion to a value as high as 145% compared with the control. On the other hand, it was confirmed that use of TGF-β2 exhibited hair elongation-suppression to a value as low as 59% compared with the control.

Accordingly, it was shown to be possible to evaluate a hair growth-regulating agent using an elongation quantity of hair at the buttocks of a pig as an indicator.

(2) Cyclosporine A

Similarly to Example 1, hair follicles at the buttocks of a pig were obtained. As a medium was used William's E medium (Sigma cat. No. W1878). One % of a penicillin/streptomycin solution (Gibco cat. No. 15140-122) was added to the William's E medium.

To the above-mentioned William's E medium was incorporated with Cyclosporine A (CsA) (Sigma cat. No. C-1832) (Taylor et al., J. Invest Dermatol. Vol. 100, 237-239 (1993)) which is confirmed to promote hair growth by an organ culture of the hair follicles of human, so that it is contained in the medium at a final concentration of 100 ng/mL, 1000 ng/mL.

The hair follicles were incubated at 37° C. for 7 days in an incubator containing 5% of $CO_2$. The medium was exchanged every two days or every three days, and a hair elongation quantity after 7 days incubation was measured and compared with that of a control.

For evaluation of the growth quantity of the hair follicles, a method similar to that of Example 1 was used.

For the control, William's E medium not containing a test substance was used, and a hair elongation quantity after the organ culture was regarded as 100%.

TABLE 3

| Test substance | Hair elongation rate (%) when that of control is regarded as 100% |
|---|---|
| CsA (100 ng/mL) | 116 |
| CsA (1000 ng/mL) | 120 |

It was confirmed that use of CsA (100 ng/mL) exhibited hair elongation promotion to a value as high as 116% compared with the control. Meanwhile, it was confirmed that use of CsA (1000 ng/mL) exhibited hair elongation promotion to a value as high as 120% compared with the control.

(3) Summary

Accordingly, it was shown to be possible to evaluate a hair growth-regulating agent using an elongation quantity of hair at the buttocks of a pig as an indicator.

What is claimed is:

1. A method for evaluating or selecting a hair growth-regulating agent for male hormone-dependent hair which comprises
    (a) collecting and isolating hair follicles from the abdominal region or a dorsal region of a pig;
    (b) culturing the hair follicles of part (a) in an organ culture in the presence of a test substance; and
    (c) measuring whether the test substance increases or decreases growth of the cultured hair follicles as compared to growth of control hair follicles from the same region that were cultured without the test substance,
    wherein growth of the cultured hair follicles is measured by determining elongation or gauge of the hair using an image analysis or a micrometer under a microscope, an increased growth of at least 16% over that of the control indicating the test substance is a hair growth-regulating agent that promotes growth of male hormone-dependent hair; and a decreased growth of at least 25% less than that of the control indicating the test substance is a hair growth-regulating agent that suppresses growth of male hormone-dependent hair.

2. A method for evaluating or selecting a hair growth agent for male alopecia which comprises
   (a) collecting and isolating hair follicles from the abdominal region of a pig;
   (b) culturing the hair follicles of part (a) in an organ culture in the presence of a test substance; and
   (c) measuring whether the test substance increases growth of the cultured hair follicles as compared to growth of control hair follicles from the same region that were cultured without the test substance,
   wherein growth of the cultured hair follicles is measured by determining elongation or gauge of the hair using an image analysis or a micrometer under a microscope, increased growth of at least 16% over that of the control indicating the test substance is a hair growth agent for male alopecia.

3. A method for evaluating or selecting a hair growth-suppressing agent for male hormone-dependent hair which comprises
   (a) collecting and isolating hair follicles from the dorsal region of a pig;
   (b) culturing the hair follicles of part (a) in an organ culture in the presence of a test substance; and
   (c) measuring whether the test substance decreases growth of the cultured hair follicles as compared to growth of control hair follicles from the same region that were cultured without the test substance,
   wherein growth of the cultured hair follicles is measured by determining elongation or gauge of the hair using an image analysis or a micrometer under a microscope, decreased growth of at least 25% less than that of the control indicating the test substance is a hair growth-regulating agent that suppresses growth of male hormone-dependent hair.

4. A method for evaluating or selecting a hair growth-regulating agent that acts without the intervention of the action of a male hormone which comprises
   (a) collecting and isolating hair follicles from the lateral region, inguinal region, shoulder or buttocks of a pig;
   (b) culturing the hair follicles of part (a) in an organ culture in the presence of a test substance; and
   (c) measuring whether the test substance increases or decreases growth of the cultured hair follicles as compared to growth of control hair follicles from the same region that were cultured without the test substance,
   wherein growth of the cultured hair follicles is measured by determining elongation or gauge of the hair using an image analysis or a micrometer under a microscope, increased growth of at least 16% over that of the control indicating the test substance is a hair growth-regulating agent that promotes growth of hair without the intervention of the action of male hormone; and decreased growth of at least 25% less than that of the control indicating the test substance is a hair growth-regulating agent that suppresses growth of hair without the intervention of the action of male hormone.

5. The method of any of claims 1-4, wherein the measuring is performed using an image analysis under a microscope.

6. The method of any of claims 1-4, wherein the measuring is performing using a micrometer under a microscope.

7. The method of claim 1, wherein the method measures whether the test substance increases growth of the cultured hair follicles.

* * * * *